United States Patent
Kling

[11] Patent Number: 5,817,086
[45] Date of Patent: Oct. 6, 1998

[54] ABSORBENT PRODUCT WITH LEAKAGE BARRIER

[75] Inventor: Robert Kling, Skene, Sweden

[73] Assignee: SCA Molnlycke AB, Goteborg, Sweden

[21] Appl. No.: 836,926

[22] PCT Filed: Dec. 28, 1995

[86] PCT No.: PCT/SE95/01595

§ 371 Date: Aug. 5, 1997

§ 102(e) Date: Aug. 5, 1997

[87] PCT Pub. No.: WO96/20674

PCT Pub. Date: Jul. 11, 1996

[30] Foreign Application Priority Data

Dec. 30, 1994 [SE] Sweden ................... 9404581

[51] Int. Cl.$^6$ ................................................. A61F 13/15
[52] U.S. Cl. ..................................... 604/385.2; 604/95
[58] Field of Search ........................... 604/373, 385.1, 604/385.2, 395, 397–398

[56] References Cited

U.S. PATENT DOCUMENTS

| | | | |
|---|---|---|---|
| 4,662,877 | 5/1987 | Williams | 604/385.2 |
| 4,892,536 | 1/1990 | DesMarais et al. | 604/385.2 |
| 4,895,568 | 1/1990 | Enloe | 604/385.2 |
| 4,990,147 | 2/1991 | Freeland | 604/385.2 |
| 5,037,416 | 8/1991 | Allen et al. | 604/385.2 |
| 5,269,775 | 12/1993 | Freeland et al. | 604/385.2 |
| 5,304,159 | 4/1994 | Tanji et al. | 604/385.2 |
| 5,304,160 | 4/1994 | Igaue et al. | 604/385.2 |
| 5,330,598 | 7/1994 | Erdman et al. | 604/385.2 |
| 5,342,342 | 8/1994 | Kitaoka | 604/385.2 |
| 5,527,302 | 6/1996 | Endres et al. | 604/385.2 |

FOREIGN PATENT DOCUMENTS

| | | |
|---|---|---|
| 568944 | 2/1986 | Australia . |
| 0 355 740 A2 | 2/1990 | European Pat. Off. . |
| 0 357 298 A2 | 3/1990 | European Pat. Off. . |
| 2 284 537 | 6/1995 | United Kingdom . |
| 9222271 | 12/1992 | WIPO ................ 604/385.2 |

Primary Examiner—John G. Weiss
Assistant Examiner—K. M. Reichle
Attorney, Agent, or Firm—Burns, Doane, Swecker & Mathis LLP

[57] ABSTRACT

The present invention relates to an absorbent product such as a diaper, a pant diaper, an incontinence shield or the like, having a front portion (13; 113; 213; 313; 413), a rear portion (12; 112; 212; 312; 412) and an intermediate crotch portion (1; 114; 214; 314; 414) further having an absorbent body (4; 404), a liquid-impermeable bottom layer (5; 105; 205; 305; 405) and a relatively easily flexible top layer (2; 102; 202; 302; 402), which, when the absorbent product is used, is intended to lie closest to the body of the user, further having an opening (17; 117; 217; 317; 417) having, viewed in the longitudinal direction of the product, a front end (18; 118; 218; 318; 418) and a rear (21; 121; 221; 321; 421) end, and two substantially longitudinal lateral edges (19, 20; 119; 120; 219; 220; 319; 320; 419, 420), and which, at least within the area of the opening, (17; 117; 217; 317; 417) is not joined to the absorbent body (4; 404). The product has an elastic tongue (24; 124; 224; 324; 424) at the rear end (21; 121; 221; 321; 421) of the opening, the rear end of the opening being located at the root (25; 125; 225; 325; 425) of the tongue. The tongue (24; 124; 224; 324; 424) is contracted in its elastically unloaded state and folded in the area of the root (25; 125; 225; 325; 425) of the tongue and the rear end (21; 121; 221; 321; 421) of the opening, whereby the tongue 24; 124; 224; 324; 424) forms a mechanical barrier (29; 429) against the transport of waste past said area.

12 Claims, 3 Drawing Sheets

ABSORBENT PRODUCT WITH LEAKAGE BARRIER

BACKGROUND OF THE INVENTION

1. Field of the Invention

The present invention relates to an absorbent product such as a diaper, a pant diaper, an incontinence shield or the like, comprising a front portion, a rear portion and an intermediate crotch portion, further comprising an absorbent body, a liquid-impermeable bottom layer and an easily flexible top layer, which in use of the absorbent product is intended to lie closest to the body of the user, which further comprises an opening having, as viewed in the longitudinal direction of the product, a front end and a rear end and two substantially longitudinal lateral edges, and which, at least within the area of the opening is not joined to the absorbent body.

2. Discussion of Related Art

Diapers with top layers provided with openings are previously known by, e.g., AU-A-45217/85 and EP-A2-0 357 298. The purpose of these designs is to achieve a diaper which isolates feces from the skin of the user. Feces which come into contact with the skin can cause skin irritation and can also make it more difficult to clean the user when diapers are changed. These patent specifications describe diapers which have elastic means attached to the top layer provided with an opening, said elastic means pulling the top layer together in its longitudinal direction and lifting it from the underlying absorbent body, which is deformed as a bowl at the same time. In this manner, a form of bowl is created with the top layer as a cover provided with an opening. Excreted feces are to be deposited through the opening and isolated from contact with the user by the top layer.

One embodiment according to EP-A2-0 357 298 is provided with an elastic means 28 in the area behind the opening 26, see, e.g., FIG. 1 in the description, col. 6, line 48–col. 7, line 1. The rear elastic means is set to force the rear piece of the top layer 24 into the "gluteal groove" between the buttocks of the user, which is said to tend to prevent feces from being transported into this area of the user's body. Such a design is, however, no guarantee that waste will not leak out by this path. In order to achieve any security at all against waste leakage, i.e. to prevent feces from being transported rearwardly over the contact surface of the top layer in the user's buttocks region, it is required that the top layer be pressed hard against the user. This is uncomfortable and can in itself give rise to skin irritation problems in a very sensitive area of the body. Even the smallest gap between the top layer and the user, e.g., due to the elastic means not being sufficiently tensioned to be able to lift the top layer up into the "gluteal groove" of the user will destroy the intended leakage barrier effect.

OBJECTS AND SUMMARY

The present invention has a purpose of achieving a leakage barrier which prevents feces from leaking out from the rear portion of the product. Furthermore, the invention is intended to achieve a leakage barrier which does not cause skin irritation to the user.

This is achieved according to the invention by virtue of the and fact that the product has an elastic tongue at the rear end of the opening, the rear end of the opening being located at the root of the tongue, and that the tongue in its elastically unloaded state is contracted and folded in the area at the root of the tongue and the rear end of the opening, whereby the tongue forms a mechanical barrier against transport of waste past said area.

The tongue will be in its contracted state when the diaper is used, by virtue of the fact that it is elastic and very flexible and that there are no forces which prevent it from returning to its elastically unloaded state. Thanks to the contraction of the tongue, the tongue material is folded at the root of the tongue, i.e. at the rear end of the opening, and there forms a physical barrier or wall which is raised above the surface of the top layer, thus effectively preventing loose and solid waste from passing the barrier. Since the tongue is elastic, the otherwise easily flexible material in the tongue will bunch up in the contracted state to a thick barrier which will seal any gap between the user and the top layer. Since the contracted tongue, when the diaper is used, does not have any elastic means, e.g. threads, which will be pressed against the body of the user, for example as in the previously mentioned EP-A2-0 357 298, a barrier will be obtained which does not irritate the skin of the user.

In a preferred embodiment of the invention, the product has a longitudinal line of symmetry, the rear end of the opening being arranged in the rear portion of the product and the tongue being centrally placed relative to the longitudinal line of symmetry of the product.

According to another preferred embodiment of the invention, the tongue extends in its extended state forward towards the front end of the opening, and has a front end and two lateral edges. In an advantageous embodiment, the respective lateral edge of the tongue, in the extended state, is parallel to the adjacent respective lateral edge of the opening within an area of the opening corresponding to the length of the tongue in its extended state. In a particularly advantageous embodiment of the invention, the tongue includes a portion of the top layer which, in the extended state of the tongue, has the same shape and size as the opening. It is thereby possible to avoid waste in material when producing the opening in the top layer, by allowing the portion of the top layer, which otherwise would have been discarded when cutting out the opening, to form the tongue.

In an additional embodiment of the invention, the tongue is essentially rectangular and the front end edge extends essentially transverse to the product. In an alternative embodiment, the tongue has the shape of a trapezoid, the root of the tongue constituting the longer of the parallel sides and the two lateral edges converging from the root of the tongue towards the front end of the tongue.

In an additional embodiment of the invention, the tongue comprises at least one elastic means disposed substantially in the longitudinal direction of the product. In a particularly advantageous embodiment of the invention, the elastic means extends further from the tongue over the top layer behind the root of the tongue. Instead of attaching elastic means to the tongue, the tongue per se can consist of an elastic material which is elastic at least in the longitudinal direction of the product.

In order to prevent the skin of the user from coming into contact with the absorbent body through the opening in the top layer, the absorbent body is preferably enclosed between the bottom layer and an inner liquid-permeable casing.

BRIEF DESCRIPTION OF THE DRAWINGS

The invention will now be described in more detail with reference to the Figures shown in the accompanying drawings, of which.

DETAILED DESCRIPTION OF THE PREFERRED EMBODIMENTS

Figure 1:
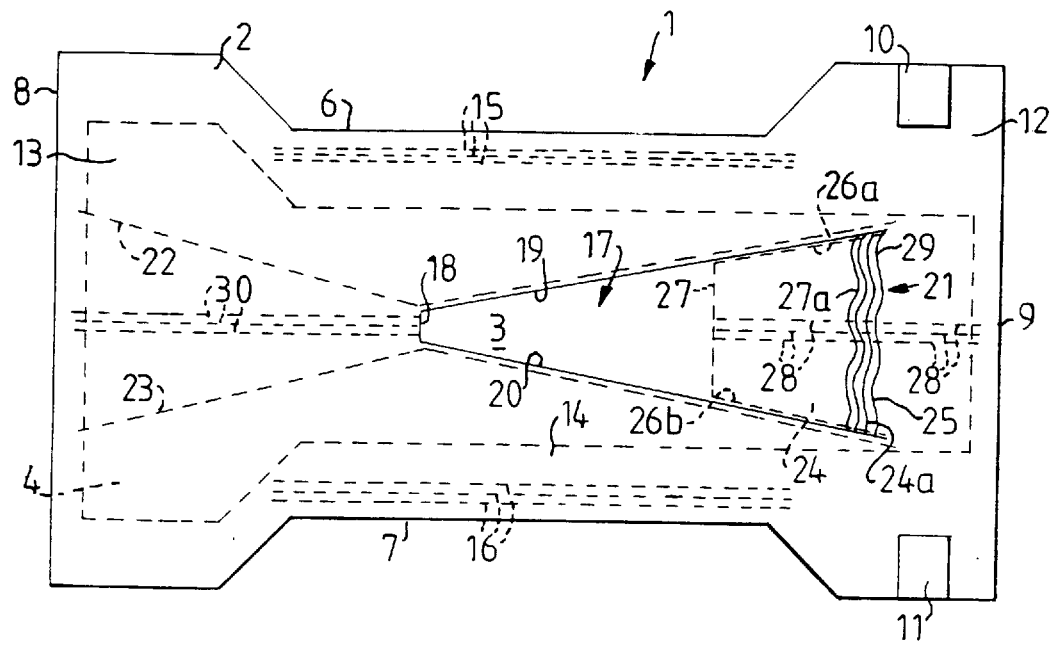
FIG. 1 shows schematically a plan view of a first embodiment of a diaper according to the invention in its extended state, but with the elastic tongue shown both in its contracted and extended states, the diaper being viewed from the side intended to receive liquid upon use.
Figure 2:
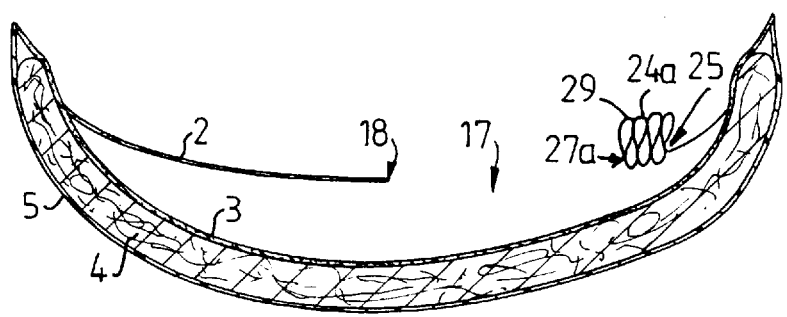
FIG. 2 shows schematically a longitudinal sectional view of the diaper in FIG. 1 in an elastically contracted state.

The diaper 1 in FIGS. 1–2 has in order viewed from the side facing the observer in FIG. 1, a liquid-permeable top layer 2, an inner liquid-permeable cover layer 3, an absorbent body 4, and a liquid-impermeable bottom layer 5.

The top layer 2, the inner liquid-permeable cover layer 3 and the bottom layer 5 all have the same shape and size and extend with edge portions outside the lateral edges of the absorbent body. The top layer 2 and the inner liquid-permeable cover layer 3 are joined to each other, for example by means of a binding agent, at their peripheral edge areas along the lateral edges 6,7 and the end edges 8,9 of the diaper, but are not joined to each other over the major portion of the area of the diaper inside the edge areas. The inner liquid-permeable cover layer 3 is joined in a conventional manner to the underlying absorbent body 4., e.g. by means of a plurality of lines of adhesive or a sparse net pattern of adhesive. In the edge area of the diaper, the inner liquid-permeable cover layer 3 is also joined to the bottom layer 5, which is in turn joined to the absorbent body 4 in the area within the edge areas, in a manner which is known per se to the person skilled in the art, by means of, for example, a number of lines of adhesive. It is, however, not necessary for the invention that the above mentioned layers have the same shape and size, and thus it is not necessary that they be joined together at the edge portions. Nor is it necessary that the absorbent body be joined to all of the layers surrounding it. The absorbent body can, for example, be removably arranged between the bottom layer and the top layer.

The top layer 2 preferably consists of a fiber fabric, so-called non-woven fabric, for example of the type thermobond or spunbond, but other fiber fabrics are conceivable. Alternatively, it can consist of a perforated thermoplastic layer, e.g. a polyethylene layer. It is also conceivable that it consists of a laminate of two or more layers. It is suitable to select a soft material since the top layer will be in contact with the skin of the user at least over portions of its surface. The inner cover layer 3 can consist of the same material as or another type of material than the top layer 2. The bottom layer 5 consists, for example, of polyethylene or polypropylene. A hydrophobisized fiber fabric is also conceivable. The bottom layer 5 can also consist of a laminate of a thermoplastic layer and a fiber fabric, or a fiber fabric extrusion-coated with a plastic film. The fiber fabric should in these cases be placed outermost so that the diaper will be given a textile look.

The absorbent body 4 can comprise any absorbent material known to the person skilled in the art, e.g. fluff pulp of cellulose fibers, preferably with superabsorbent polymers mixed in, i.e. polymers capable of absorbing many times their own weight in liquid. The absorbent body 4 can consist of one or more absorbent layers, which can differ in shape and size, even between themselves. Examples of conceivable shapes are rectangular or hourglass-shaped. The absorbent layers can be made of the same or different types of absorbent material and have different absorbent properties and functions. In FIG. 1, the diaper 1 is shown in an hourglass shape and the absorbent body is T-shaped. It is also conceivable that the diaper have another shape than the hourglass shape, e.g. a rectangular shape or T-shape.

The diaper is also provided with a fastening system of a type which is well known to the person skilled in the art, schematically illustrated by two fastening tabs 10,11 arranged at the rear portion 12 of the diaper. The rear portion is the portion of the diaper which in use is intended to be in contact with the buttocks of the user. The fastenings tabs 10,11 comprise a mechanical fastening means, e.g. a VELCRO lock or an adhesive fastening means, for cooperation with a receiving area at the front portion 13 of the diaper, when the diaper is placed on the user. The receiving area is not shown in FIG. 1, but can, for example, consist of an area of the bottom layer, possibly also of a separate strip applied to the outside of the bottom layer, within the area of the diaper's front portion within which the fastening tabs are intended to be fixed when the diaper is put on the user. The receiving area must of course be adapted to the fastening means used. If, for example, VELCRO, so-called hooks and loops, are used, the receiving area can consist of a portion of fiber fabric or one or more strips or pieces of fiber fabric, where the fibers in the fiber fabric constitute the fastening elements to which the hooks of the VELCRO can engage when closing the diaper. For the sake of completeness, it may be mentioned that the fastening system does not necessarily have to comprise fastening tabs. Rather the tabs can be replaced by receiving areas placed on either the top or bottom layer of the diaper, preferably the top layer, as well as at the rear portion of the diaper.

Between the rear portion 12 and the front portion 13, there is a crotch portion 14. There are no strict boundaries for the transition between the three portions, but the crotch portion is the portion of the diaper which, in use, is intended to be placed between the user's legs against the crotch. In order to prevent liquid from running out over the lateral edges 6,7 of the crotch portion 14, the diaper is equipped with elastic means 15,16 along said edges 6,7. Such elastic means are common in diapers and, in addition to preventing liquid leakage, provide a good diaper fit.

The elastic means 15,16 are stretched straight in the longitudinal direction of the diaper, but can also be disposed in various curved shapes, but always extending essentially in the longitudinal direction of the diaper. This means a direction which deviates at most 45° from the longitudinal line of symmetry of the diaper. The elastic means 15,16 each consist in the example of FIG. 1 of three elastic threads, but the number of elastic means can be both greater or less. The elastic means can consist of rubber threads, but it is also conceivable to use elastic foam, fiber fabric, net, tapes or films. The elastic means 15,16 are applied between the bottom layer 5 and the inner cover layer 3, and are joined thereto by means of adhesive, for example. It is also conceivable that the elastic means 15,16 be mounted between the top layer 2 and the inner cover layer 3, and be joined therebetween in a similar manner.

An opening 17 arranged symmetrically relative to the longitudinal line of symmetry of the diaper is disposed in the top layer 2. The front end 18 of said opening is located between the wetting point and the defecation point. The wetting point refers to the area of the diaper within which urine emission is expected to occur if the diaper is put on properly, and the defecation point refers to the area within which feces are deposited if the diaper is put on correctly, i.e. the areas right in front of the urethral opening and the anus, respectively, of the user, taking into account normal variations of the anatomy of the user, within the size interval of the user for which the diaper is dimensioned. The lateral edges 19,20 of the opening 17 diverge from each other towards the rear portion 12 of the diaper, and the rear end 21 of the opening is located in the rear portion somewhat from the rear end of the absorption body.

Two elastic means 22,23, for example threads, are fixed in an extended state to the top layer 2 and run from the front of the front portion 13 of the diaper to the rear of the rear portion 12 of the diaper. The threads 22,23 converge towards each other from the front portion 13 to the front end 18 of the opening, and then run along the lateral edges 19,20 of the opening approximately to the rear end 21 of the opening. In the embodiment shown, the elastic threads 22,23 are applied with the aid of narrow strips (not shown) of fiber fabric, which are fixed by gluing or another suitable manner, to the threads and the top layer. In the embodiment shown, the strips are arranged along the entire length of the threads and they are thus fixed to the top layer along their entire lengths. This is, however, not necessary. Rather, the threads can be fixed to the top layer only at their ends and on either side of the front end of the opening. It is also possible to fix the threads directly to the top layer, using the technology described in Swedish Patent Application 9304232-3, filed on 21 Dec. 1993. This application describes how elastic elements can be bonded directly to an underlying substrate with the aid of thermoplastic components, which are locked to the elastic elements by mechanical locking or chemical adhesion, and which are bonded to the underlying substrate, preferably by ultrasonic welding. Further details are contained in said Swedish patent application.

The purpose of arranging the elastic means 22,23 in the is manner described above, is, with a high degree of security, to keep the lateral edges 19,20 apart during the use of the diaper so that the desired width of the opening is maintained. FIG. 2 shows the configuration which the diaper assumes when it is deformed under the influence of the contraction of the elastic means from the extended to the contracted tensionless state. The top layer 2 is folded and shortened, thus curving the absorbent body 4 and the other layers 3,5. The top layer 2 will thereby be lifted up so that it will be spaced from the absorbent body 4 and the inner cover layer 3. Further details and advantages of the arrangement of the opening 17 and the elastic means 22,23 along the opening 17 are described in more detail in Swedish Patent Application 9304132-5, filed on 13 Dec. 1993, to which reference is hereby made.

From the rear end 21 of the opening, a tab or tongue 24 extends forward towards the front end 18 of the opening. FIG. 1 shows the tongue 24 both in its contracted state 24a, illustrated with a number of solid wave lines, and in its extended state 24, illustrated by dashed contour lines. The tongue 24 has the shape in the extended state of a trapezoid.

The root 25 of the tongue is located at the rear end 21 of the opening and constitutes the longer of the parallel sides of the trapezoid. The rear end of the opening is the line extending between the points at which the lateral edges 19,20 of the opening end at the rear portion of the opening. Said line would have been the end edge of the opening, had there been no tongue. The longitudinal lateral edges 26a,26b of the tongue in the extended state extend parallel to the respective adjacent lateral edge 19,20 of the opening 17. The tongue has a front end 27,27a extending in the transverse direction of the diaper. The front end 27 of the tongue is parallel to and shorter than the root 25 of the tongue. Thus, as can be seen in FIG. 1, the tongue 24 tapers towards its front end 27. As regards manufacturing, this is advantageous since the tongue 24 can be cut out at the same time as the opening 17 is cut out of the top layer 2, by allowing the transverse rear cut to be arranged somewhat in front of the rear end points of the longitudinal cuts. In principle, the cutting tool can have the shape of the letter A. It is thereby possible to save materials, since the portion of the top layer which is cut out when cutting the opening 17 is normally discarded. By virtue of the present invention, a major portion thereof can be used to form the tongue 24. It is now only that portion of the top layer material within the enclosed region of the "A" which will go to waste.

Elastic means 28 are mounted in a pretensioned state over the tongue in the longitudinal direction of the diaper and the tongue. These elastic means 28 also extend backwards towards the rear end 9 of the diaper from the tongue 24 in over the top layer 2 behind the root 25 of the tongue. Within the extended area of the tongue 24, the elastic means 28 are shown as dot lines which are direct continuations of the dashed lines 28. The elastic means 28 will, as soon as the top layer material in front of the tongue has been cut away, contract the tongue to the folded and collected configuration shown in FIGS. 1 and 2. "Folded" in this case means any type of material bunching, regular or irregular, caused by the contraction of the tongue. The folds can for example consist of a plurality of wrinkles. By collecting the tongue material within a relatively limited area, it will form a barrier 29, with a certain height, at the rear end 21 of the opening. This is shown most clearly in FIG. 2. Thanks to the fact that the opening is placed centrally relative to the longitudinal line of symmetry of the diaper, the tongue 24 and the barrier 29 will be placed centrally in an area of the diaper which is designed during use to be in the seat region between the buttocks of the user. Since the tongue 24 is also made of a relatively easily flexible material, e.g. of fiber fabric, and the tongue 24 comprises elastic means, the barrier 29 will be folded and contracted to a sufficient height and extent to function as a seal against transport of waste past the area at the root 25 of the tongue and the rear end 21 of the opening, and will prevent loose and solid waste from penetrating into the "gluteal groove" in the seat region between the buttocks of the user. When using the diaper, it will be pressed against the body of the user, and the various diaper components will be subjected to a pressure from the body of the user. Due to the anatomy of the user, at least a central portion of the barrier 29, within the area between the buttocks of the user, will be relatively unloaded, i.e. not be subjected to any major forces from the user. This force is instead absorbed by the area of the diaper to one side of the central portion of the barrier, which when the diaper is used will be in tight contact against the buttocks of the user. The width of the barrier will, of course, have importance for how large a portion thereof is unloaded or compressed. If only the barrier is centrally placed relative to the longitudinal line of symmetry of the diaper, at least a central portion of the barrier will always be located within in the relatively unloaded area between the buttocks of the user. It is also noted that, since the barrier 29 is formed of the tongue 24, which is in turn formed by a portion of the top layer 2, the barrier is suitably made of a soft material so that any compressed end portions of the barrier will not cause any discomfort or skin irritation for the user.

In order to obtain the desired sealing effect of the barrier, it has proved important that the spring force of the elastic means 28 be great enough so that the tongue 24 will be contracted to a length which is less than the half of the fully extended length of the tongue. The spring force must, of course, be adjusted to the type of elastic material and to the type of top layer material being used.

It is also important that the elastic means 28 continue past the root 25 of the tongue over the top layer behind the root of the tongue. This provides a tensile force which acts on the tongue 24 at the root 25 of the tongue. Furthermore, the root 25 of the tongue is reinforced by the elastic means 28. In summary, the elastic means 28 hold the tongue level with the top layer 2, with portions of the tongue folds above the top layer.

From the front end 18 of the opening, elastic means 30 applied in a pretensioned state, extend towards the front end edge 8 of the diaper. These elastic means 30 are aligned with the elastic means 28 behind the opening 17. This has advantages for the manufacturing processes, since the front and the rear elastic means 28,30 can be cut from the same continuous string of elastic means, which, prior to cutting out the opening 17 and the cutting of the tongue 24, runs continuously longitudinally across a central portion of the top layer 2.

The front and rear elastic means 28,30 are preferably applied to the underside of the top layer 2, for example, in a manner similar to that described previously for the elastic means 22,23, along the lateral edges of the opening. The same applies, of course, also to the selection of alternative elastic materials.

An alternative to using elastic means to elastify the tongue 24 is to make the top layer, at least within portions around the opening 17, of a pretensioned elastic material. In the same manner as is described above, the tongue can be folded up at the root, by virtue of the fact that the elastic material strives to return to its elastically untensioned state when the tongue has been cut.

FIGS. 3–7 show alternative embodiments of a diaper according to the invention. Components in these embodiments corresponding to the embodiment according to FIG. 1 have been given the same reference numerals, but preceded by different numerals in the hundred's place. Components in the embodiment of FIG. 3 have numerals beginning with 100, components in the embodiment of FIG. 4 have numerals beginning with 200, etc. For the sake of clarity, no absorbent body has been drawn in FIGS. 3–6. It is, however, also self-evident that such an absorbent body is arranged in these diapers as in the diaper according to FIG. 1. To avoid unnecessary repetitions, only essential differences between the embodiments according to FIGS. 3–7 and according to FIGS. 1–2 will be described below. Otherwise, reference is made to the preceding description.

Figure 3:
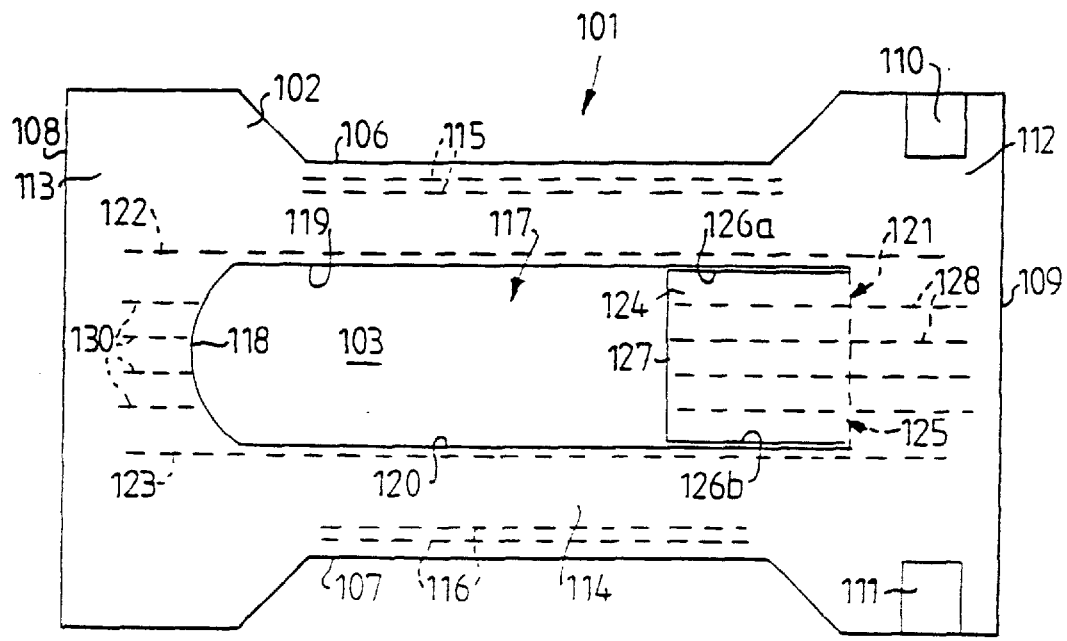
FIG. 3 shows schematically a plan view corresponding to the view of FIG. 1, except that the absorbent body is not shown and that the tongue is only shown in its extended state, of a second embodiment of a diaper according to the invention.

The diaper 101, shown in FIG. 3, differs from that shown in FIG. 1 by virtue of the fact that the lateral edges 119,120 of the opening are parallel and extend entirely in the longitudinal direction of the diaper 101. The front end 118 of the opening 117 is arcuate. The opening 117 is, compared to the opening 17 in FIG. 1, longer and extends somewhat into the front portion 113 of the diaper.

The elastic means 128, which are mounted over the tongue 124 and behind the opening 117, and the elastic means 130 in front of the opening 117 are mounted with a greater spacing between the individual threads. The elastic means 128 can thus act over a larger width of the tongue 124.

The tongue 124 has an essentially rectangular shape in view of the fact that the lateral edges 126a,126b of the tongue, as is the case in FIG. 1, are parallel to the respective adjacent lateral edges 119,120 of the opening 117.

Figure 4:
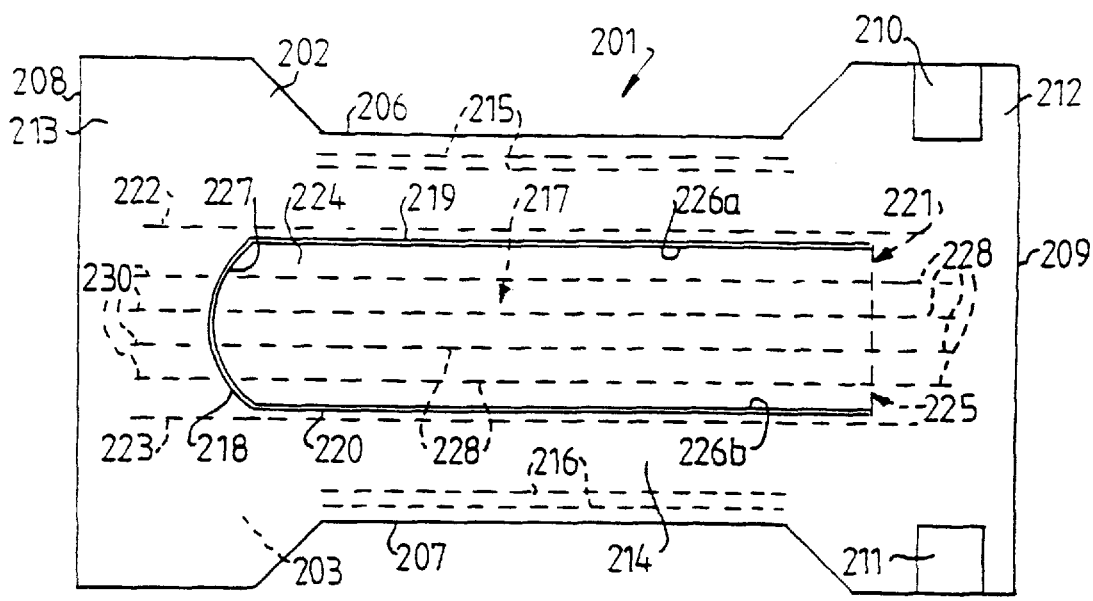
FIG. 4 shows schematically a plan view corresponding to the view in FIG. 3, of a second embodiment of a diaper according to the invention.

The diaper 201 in FIG. 4 is similar to the diaper 101 in FIG. 3, but with the difference being that the tongue 224 has the same shape and size as the opening 217. In this manner, no material is wasted when cutting the opening 217. Rather, all top layer material can be used to form the tongue 224.

Figure 5:
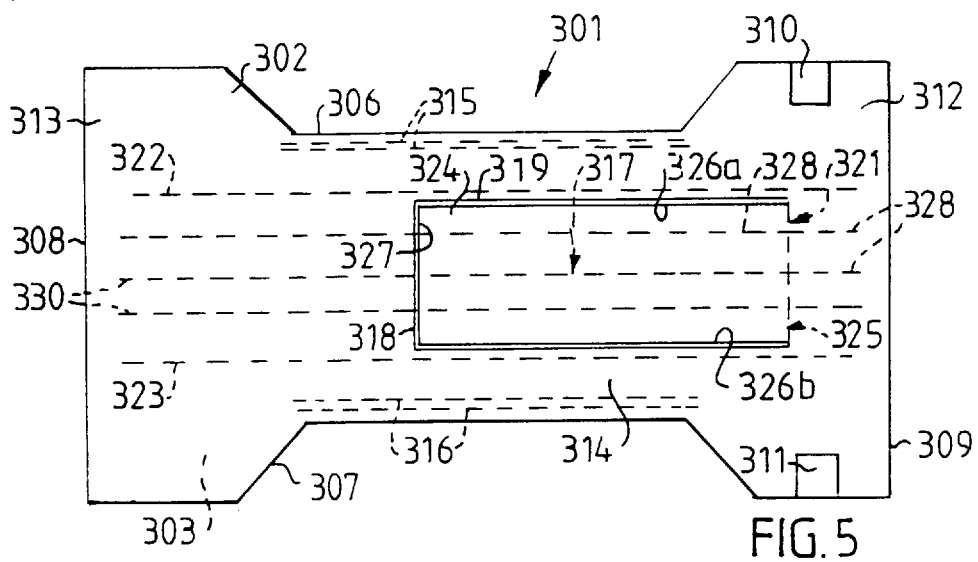
FIG. 5 shows schematically a plan view corresponding to the view in FIG. 3, of a fourth embodiment of a diaper according to the invention.

FIG. 5 shows a diaper 301 which, as is the case with the diaper 201 in FIG. 4, has a tongue 324 which is substantially rectangular and fills up the entire opening 317 in its extended state. The difference is that the opening 317, and thus the tongue 324, are shorter than the corresponding component in FIG. 4. An additional difference is that the front end 318 of the opening and the front end 327 of the tongue are straight and not curved. The front end 318 of the tongue extends substantially in a transverse direction of the product.

Figure 6:
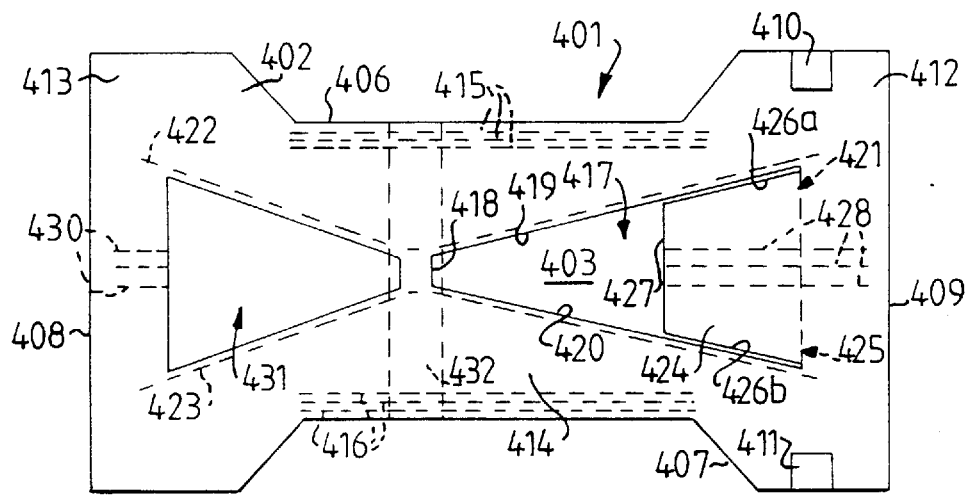
FIG. 6 shows schematically a plan view corresponding to the view in FIG. 3, of a fifth embodiment of a diaper according to the invention.
Figure 7:
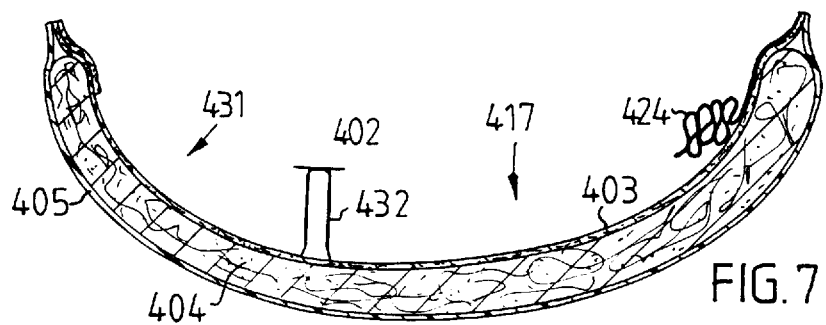
FIG. 7 shows schematically a longitudinal sectional view of the diaper in FIG. 6, when it is in an elastically contracted state.

FIGS. 6–7 show an embodiment which differs somewhat more from the other embodiments. The diaper 401 has an elastic tongue 424 similar to the tongue 24 in FIG. 1. The opening 417 is also similar to the opening 17 in FIG. 1. However, there is an additional opening 431 in the front portion 413. Between the two openings 417,431, there is a transverse dividing wall 432, between the top layer 402 and the inner liquid-permeable cover layer 403. It is intended that urine should pass through the front opening 431 down to the inner cover layer 403, to thereafter be absorbed by the underlying absorbent body 404 (see FIG. 7). The transverse dividing wall 432 is liquid-impermeable and is intended to prevent urine from running backwards along the inner cover layer 403, and at the same time to prevent feces from running or otherwise moving forwards in the diaper. The dividing wall 432 thus creates two separate containers between the top layer 402 and the inner cover layer 403, and thus prevents urine and feces from being mixed, which is an advantage since it could otherwise give rise to increased skin irritation.

Since the top layer 402 according to this embodiment has a front opening 431 for receiving urine, it is not necessary that the top layer be liquid-permeable but can instead be liquid-impermeable. The same is true of the elongated openings 117 and 217, respectively, in FIGS. 3 and 4, respectively, which both extend into the front portion 113, 213, respectively, of the respective diaper and thus permit passage of urine through the openings.

The dividing wall 432 has the shape of a tubular body, as is best seen in FIG. 7, and is fixed in narrow longitudinal portions at its respective ends to the inner cover layer 403 and the top layer 402, for example by means of adhesive. The dividing wall can, for example, consist of a polyethylene layer. For more details and advantages of this embodiment, reference is made to our Swedish Patent Application 9400916-4 filed on 18 Mar. 1994.

The embodiments of the invention described can, of course, be modified further within the scope of the invention. The invention is therefore not considered to be limited to anything other than the scope of the accompanying patent claims.

For example, the tongue can consist of a separate strip or the like applied on top of the top layer, instead of a portion cut from the top layer and integral therewith. One end of the strip can be applied to the rear end of the top layer opening, and the front edge and the larger portion of its lateral edges are free and extend from the rear end of the opening and forward. The strip has elastic means or consists of elastic material in a manner corresponding to that described above for those tongue examples shown in the Figures. In a similar manner thereto, the strip can be contracted and folded and thus form the desired barrier at the rear end of the opening. This embodiment has, however, not the material-saving advantages described for the embodiments shown.

I claim:

1. An absorbent product comprising a longitudinal direction,:

a front portion, a rear portion, an intermediate crotch portion, a liquid-impermeable bottom layer, a flexible top layer, which, in use of the absorbent product, is intended to lie closest to a body of a user, an absorbent body between said top and bottom layers, the flexible top layer includes an opening having, as viewed in the longitudinal direction of the product, a front end and a rear end and two substantially longitudinal lateral edges, and, at least within the area of the opening, the flexible top layer is not joined to the absorbent body, an elastic tongue at the rear end of the opening, the rear end of the opening being located at a root of the tongue, and the tongue in its elastically unloaded state is contracted and folded in an area at the root of the tongue and the rear end of the opening, whereby the tongue forms a mechanical barrier against transport of waste past the area at the root.

2. The absorbent product according to claim 1, wherein the product has a longitudinal line of symmetry, the rear end of the opening is arranged in the rear portion of the product, and the tongue is centrally arranged relative to the longitudinal line of symmetry of the product.

3. The absorbent product according to claim 1, wherein the tongue extends in an extended state forward towards the front end of the opening and has a front end and two lateral edges.

4. The absorbent product according to claim 3, wherein a respective one of the lateral edges of the tongue in the extended state, is parallel to a respective adjacent one of the lateral edges of the opening within the area of the opening.

5. The absorbent product according to claim 4, wherein the tongue in the extended state has a same shape and size the same as a shape and size of the opening.

6. The absorbent product according to claim 3, wherein the tongue is substantially rectangular and that an edge of the front end of the tongue extends essentially in a transverse direction of the product.

7. The absorbent product according to claim 3, wherein the tongue has a shape of a trapezoid, the root of the tongue constitutes a longer of two parallel sides and the two lateral edges converge in a direction from the root of the tongue towards the front end of the tongue.

8. The absorbent product according to claim 1, wherein the tongue comprises a portion of the top layer.

9. The absorbent product according to claim 1, wherein the tongue comprises elastic means disposed substantially in the longitudinal direction of the product.

10. The absorbent product according to claim 9, wherein the elastic means continue from the tongue in over the top layer behind the root of the tongue.

11. The absorbent product according to claim 1, wherein the tongue includes an elastic material acting elastically at least in the longitudinal direction of the product.

12. The absorbent product according to claim 1, wherein the absorbent body is enclosed between the bottom layer and an inner liquid-permeable cover layer arranged inside the top layer.

* * * * *